United States Patent [19]

Reiner

[11] Patent Number: 5,030,738
[45] Date of Patent: Jul. 9, 1991

[54] SYNTHESIS OF ANTIULCER COMPOUNDS

[75] Inventor: Alberto Reiner, Cantu, Italy

[73] Assignee: Janus Farmaceutici S.r.l., Rome, Italy

[21] Appl. No.: 527,680

[22] Filed: May 22, 1990

Related U.S. Application Data

[63] Continuation of Ser. No. 420,698, Oct. 11, 1989, abandoned, which is a continuation of Ser. No. 148,212, Jan. 27, 1989, abandoned.

[30] Foreign Application Priority Data

Mar. 28, 1986 [IT] Italy ................. 19930 A/86
Nov. 19, 1986 [IT] Italy ................. 22389 A/86

[51] Int. Cl.$^5$ ............................. C07D 407/12
[52] U.S. Cl. ............................. 549/535; 544/390;
546/197; 546/226; 548/342; 548/538; 549/441;
549/494; 549/495; 564/47; 564/58; 564/252
[58] Field of Search ............ 549/435, 441, 494, 495;
548/342, 538; 546/197, 226; 544/390; 564/47,
58, 252

[56]  References Cited
U.S. PATENT DOCUMENTS 3,957,774  5/1976  Kolopissis et al. ............ 260/246 B
4,279,819  7/1981  Price et al. ..................... 549/494
4,399,294  8/1983  Bays et al. ..................... 549/495

FOREIGN PATENT DOCUMENTS 8303435  5/1984  Netherlands .
2104071  3/1983  United Kingdom .

OTHER PUBLICATIONS

Moimas et al., Synthesis, No. 5 (1985), pp. 509–510.
Palomo et al., Chemical Abstracts, vol. 94 (1981), 46808m.
Kraemer et al., Chemical Abstracts, vol. 105 (1986), 114,968p.

Primary Examiner—Richard L. Raymond
Attorney, Agent, or Firm—Armstrong, Nikaido, Marmelstein, Kubovcik & Murray

[57]  ABSTRACT

To synthesize molecules with antiulcer action, specifically ranitidine, niperotidine and cimetidine, having the formula:

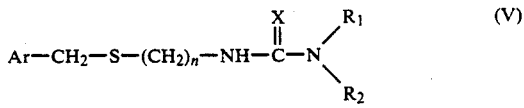

wherein $R_1$ is hydrogen or together with $R_2$ represents the rest of a cycloaliphatic or heterocyclic optionally substituted ring with 5 or 6 carbon atoms, $R_2$ represents H, alkyl, alkyl substituted with a simple or substituted aromatic ring or with a single or substituted heterocyclic ring, Ar represents a simple or substituted phenyl group, a simple or substituted heterocyclic aromatic group, $N = 1, 2, 3, 4, 5$ or $6$ and X represents CH—NO$_2$, S, N—C≡N, the compound (II) is prepared through the following process sequence:

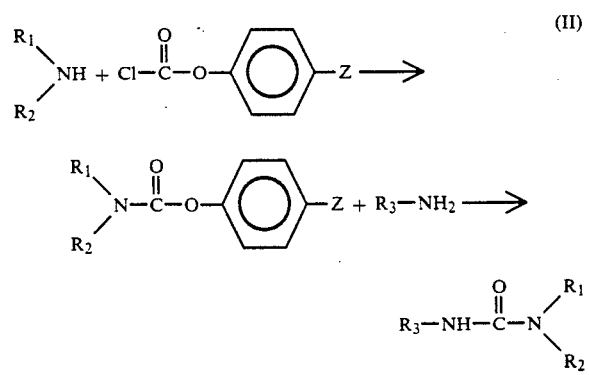

wherein Z=H, NO$_2$, halogen and $R_3 = -(CH_2)_n$ Ar, $-(CH_2)_n$—SH, $-(CH_2)_n$—S—S—$(CH_2)_n$, $-(CH_2)_n$—S—CH$_2$Ar Y being halogen.

The urea of formula

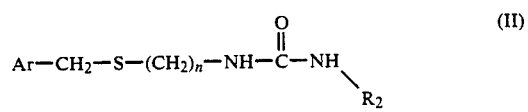

is converted in a first stage into the corresponding carbodiimide

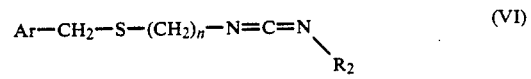

by reaction with triphenylphosphine and bromine in the presence of a strong base and in a second stage is obtained the desired compound by reaction with nitromethane or with a saline derivative of cynamide.

22 Claims, No Drawings

SYNTHESIS OF ANTIULCER COMPOUNDS

This application is a continuation of application Ser. No. 420,698 filed Oct. 11, 1989, now abandoned, which is a continuation of application Ser. No. 148,212 filed Jan. 27, 1989, now abandoned.

The present invention relates to a process for the synthesis of compounds with antiulcer action, having the following general formula:

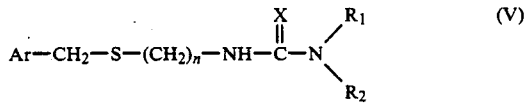

wherein $R_1$ is hydrogen or together with $R_2$ represents the rest of a cycloalophatic or heterocyclic possibly substituted ring having 5 or 6 carbon atoms, $R_2$ represents hydrogen, alkyl, alkyl substituted with a simple or substituted aromatic ring or a single or substituted heterocyclic ring, Ar represents an aromatic ring or a single or substituted heterocycle, $n=1, 2, 3, 4, 5$ or $6$ and X represents $CH-NO_2$, $S, N-C\equiv N$. Compounds covered by the above general formula and which are well known include:

(1) ranitidine, for which in the above formula:

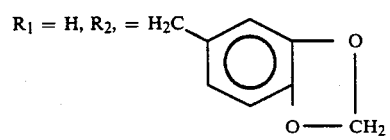

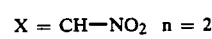

(2) niperotidine, for which:

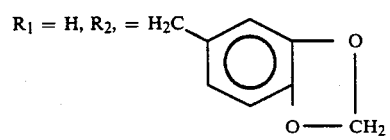

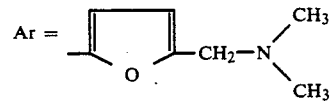

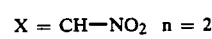

(3) cimetidine, for which:

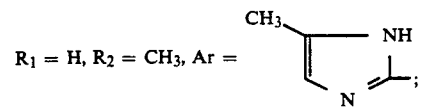

The preparation of these compounds in an industrially profitable manner is therefore of evident interest.

This method is characterized by a common starting intermediate obtained in accordance with the following synthesis scheme

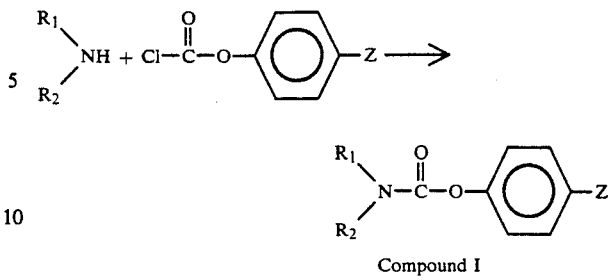

Compound I wherein
$R_1 = H$,
$R_2 =$ alkyl, substituted alkyl as for example a methyl substituted with a simple or substituted aromatic ring or with a simple or substituted heterocyclic ring;
$R_1$ and $R_2$ can also represent the rest of an cycloaliphatic or heterocyclic optionally substituted ring with 5 or 6 atoms such as for example piperdine, piperazine, pyrrolidine;
$Z = H$, $NO_2$, halogen.

This preparation takes place by reaction in an organic solvent or a mixture of organic solvents, e.g. chloroform or pyridine, in the presence of a base, at a temperature of between 0° and 25° C., the reaction mixture being subjected to stirring for 4–20 hours.

Compound (I), as a function of the substitutent Z, is isolated or utilized in the next passage (synthesis of compound II) without isolation; indeed, for $Z = NO_2$ the intermediate is hydrolabile and hence sensitive to humidity.

Compound (I) is then reacted with a second amine leading to a disubstituted urea in accordance with the following scheme:

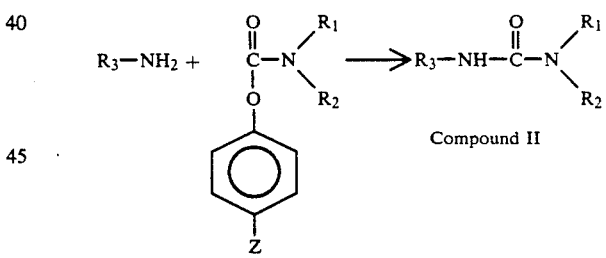

Compound II wherein $R_1$ and $R_2$ have the above indicated meanings.
$R_3 = -(CH_2)_n Ar$, $-(CH_2)_n-SH$, $-(CH_2)_n-Y$, $-(CH_2)_n-S-CH_2Ar$ wherein $n = 1,2,3,4,5,6$
Ar = phenyl or substituted phenyl group, aromatic heterocyclic or substituted aromatic heterocyclic group
Y = alogen.

From the compound (II), when $R_1 = H$ the derivatives of formula (V), are obtained through two further process steps, namely:

(a) reaction of the urea of the formula:

with a compound capable of converting it into the corresponding carbodiimide of the formula:

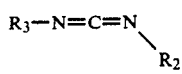
(VI)

in the presence of an acid acceptor and (b) reaction of the carbodiimide of formula (VI) with a compound selected from between nitromethane in the presence of a strong base and a saline derivative of the cyanamide to form the corresponding compound (V).

As is appears from the above schematization the process in accordance with the invention makes it possible to obtain directly, depending on the meaning of $R_2$, and Ar, either ranitidine or niperotidine, when in the second stage nitromethane is used in the presence of a strong base, or cimetidine if in the second stage a saline derivative of cyanamide is used.

The process according to the invention can be thus represented by the following synthesis scheme:

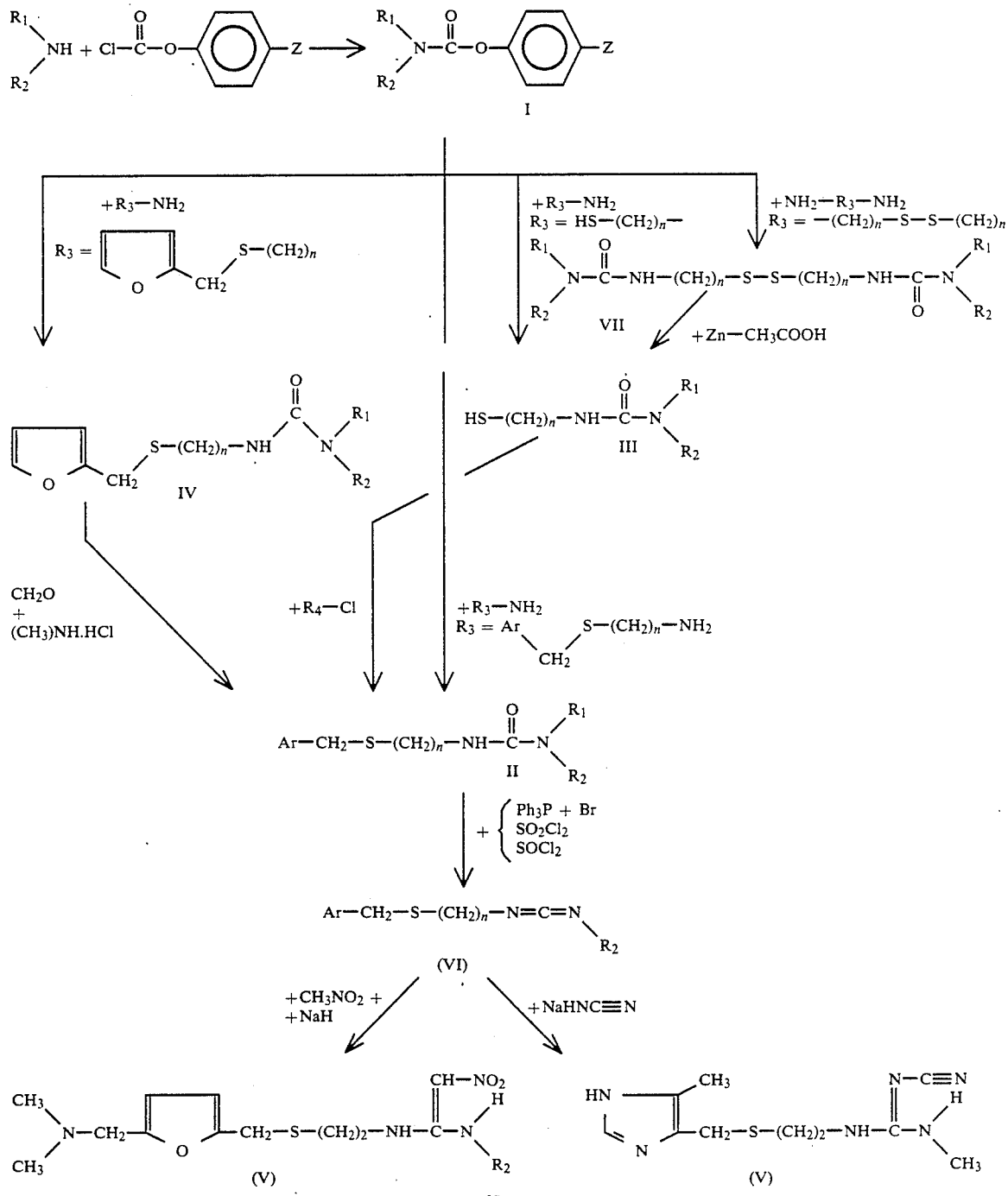

Examples of the compounds obtainable by the process described in the present invention are specifically:

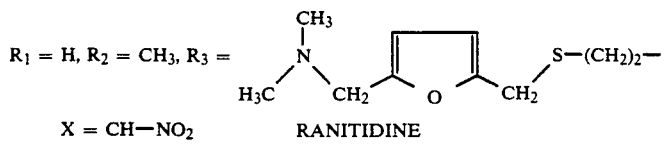
R₁ = H, R₂ = CH₃, R₃ = [structure]
X = CH—NO₂    RANITIDINE

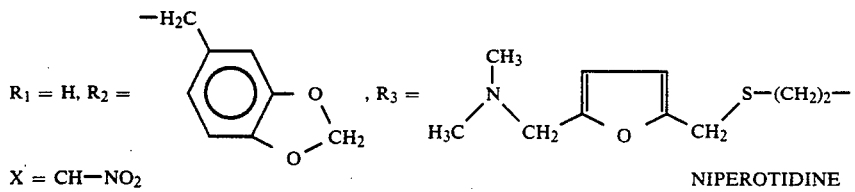
R₁ = H, R₂ = [structure], R₃ = [structure]
X = CH—NO₂    NIPEROTIDINE

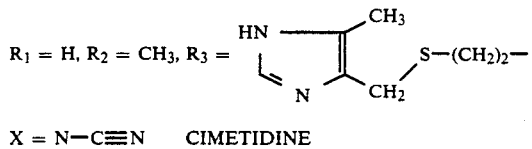
R₁ = H, R₂ = CH₃, R₃ = [structure]
X = N—C≡N    CIMETIDINE

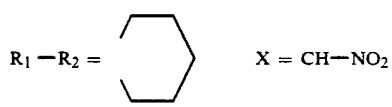
R₁—R₂ = [cyclohexyl]    X = CH—NO₂

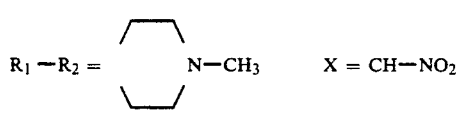
R₁—R₂ = [N—CH₃ piperazinyl]    X = CH—NO₂

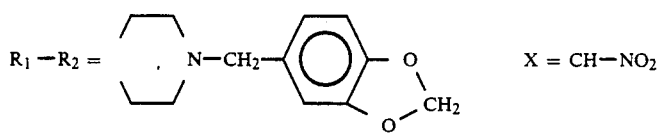
R₁—R₂ = [piperazinyl-CH₂-benzodioxole]    X = CH—NO₂

In the above compounds, when R₁ is different from hydrogen, the last two steps of the process shall be correspondingly different.

According to a first embodiment of the process of the present invention, the preparation of compound (iI) takes place by reaction of compound (I) with an amine of formula R₃—NH₂ in which R₃=—(CH₂)ₙ—SH, such as for example cysteamine (n=2), 3-mercapto-propionyl-amine (n=3), and cistamine whereby compound (III) is obtained.

The reaction is carried out in an organic solvent, preferably pyridine or in mixtures of an organic solvent and water, especially when the amine is water soluble.

The reaction is carried out at temperatures between room temperature and the boiling temperature of the solvent. Preferably the reaction is carried out at temperatures on the order of 50°-60° C., for 4-20 hours depending on the temperature and type of the amine, a compound being obtained of the formula:

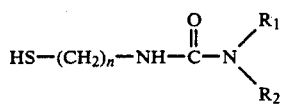
(III)

In the case of cistamine, to be used when problems of by-products might arise owing to the presence of the —SH— group, the compound (I) is firstly reacted with cistamine

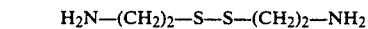
H₂N—(CH₂)₂—S—S—(CH₂)₂—NH₂ preferably in pyridine at a temperature of 40°-50° C., leading to the compound (VII). The latter, by reduction with metal zinc and acetic acid, is converted to the compound (III). Also compound (VII), as an intermediate, is novel and is an object of the present invention.

The precipitated reaction product (III) is purified by the usual methods and reacted, after activation with an appropriate base such as for example sodium hydride, in polar solvent, preferably dimethylformamide or low boiling point aliphatic alcohols, while hot and being stirred with 5-(N,N'-dimethylaminomethyl)-2-chloromethyl-furan to give the following compound:

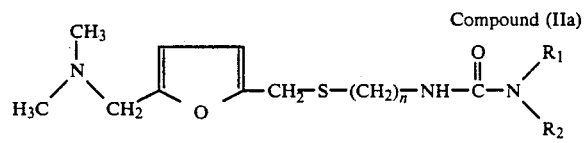
Compound (IIa)

that is compound (II) with

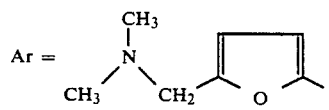
Ar =

The same reaction, if carried out on compound (IV) with 5-methyl-4-chloromethyl-imidazole leads to the intermediate:

Compound (IIc)

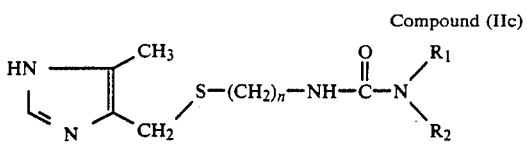

i.e. compound (II) where

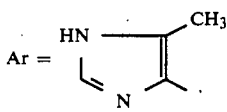

According to a second embodiment of the process of the invention the preparation of compound (II) starting from compound (I) takes place with an amine $R_3$—$NH_2$ wherein $R_3$=—$(CH_2)_n$—$S$—$CH_2$—$Ar$, where Ar, as already stated, represents:

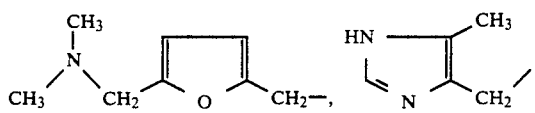

An example of such an amine is represented by:

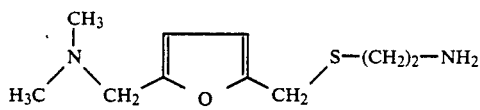

The reaction is carried out in polar organic solvent at temperatures which vary from room temperature to the boiling point of the solvent, usually on the order of 50°-60° C. Reaction times vary from 4 to 20 hours depending on the temperature and the nature of the amine. The product obtained (II) is isolated and purified in accordance with the usual techniques and then reacted as hereinafter described to give the disired final compounds. According to third embodiment of the process of the invention, compound (I) is reacted with an amine $R_3$—$NH_2$, where $R_3$=

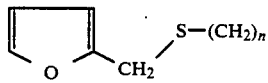

leading to the compound (IV) of the formula:

Compound (IV)

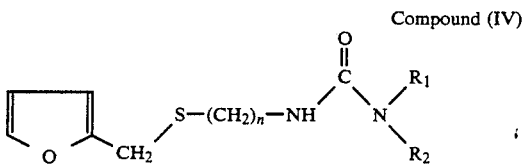

This reaction is performed by the same method described above in the second embodiment.

The reaction product (IV) is isolated and reacted with dimethylamine hydrochloride and formaldehyde in an anhydrous alcoholic medium for a period of between 4 and 20 hours at the reflux temperature of the alcoholic obtaining compound (IIa) as mentioned above.

Now considering in detail the conversion of the intermediate (II) into the desidered final compounds according to the present invention, it is pointed out first that the reactants capable of converting urea (II), wherein $R_1$=H, into the corresponding carbodiimide (VI) are selected from among triphenylphosphine $Ph_3P$, sulfuryl chloride $SO_2Cl_2$ and thionyl chloride $SOCl_2$. In the case of triphenylphosphine bromide must be present and in all cases an acid acceptor must be present, preferably an organic base and still more preferably triethylamine.

The reaction solvent is an aprotic solvent, preferably a chlorinated hydrocarbon such as dichloromethane, chloroform and others, capable of dissolving the urea (II).

The reaction is made to occur at low temperature and is carried out by introducing very slowly at a temperature on the order of 5° C. a solution of urea (II) in the reaction solvent in a reaction medium already formed in the reactor starting from the compound selected from among triphenylphosphine, thionyl chloride or sulfuryl chloride, dissolved in the reaction solvent, with the addition of bromine if necessary and of the acid acceptor, in particular triethylamine.

The aforesaid reaction medium is also formed at low temperature, specifically below 0° C. while introducing slowly the several reactants. Upon the urea (II) has been added the reaction is completed in approximately 2 hours at a temperature of between 5° and 10° C. with good yields, whereafter the carbodiimide is isolated in a known manner.

Preferably the reaction medium in which the urea (II) is introduced is in excess of the amount stoichiometrically necessary for the conversion. In the second reaction stage, when it is desired to prepare ranitidine or niperotidine, the carbodiimide (VI) in solution in a polar aprotic solvent, preferably dipolar such as dimethylformamide and dimethylsulfoxide, is added slowly to a solution of nitromethane in the same solvent prepared previously and containing a strong base such as for example sodium hydride.

The nitromethane has preferably a molar excess over the carbodiimide. Once addition of the latter is terminated, the reaction mixture is heated to a temperature of 75°-80° C. and the reaction is completed in approximately 2 hours with quantitative yields if the reactants are free of impurities. If it is desired to prepare cimetidine the compound (VI) is reacted with a saline derivative of cyanamide, preferably the sodium salt.

As appears clearly from the following examples and the preceding general considerations, the process according to the invention is firstly characterized by preparation of a novel intermediate, i.e. the ureic precursor (II), which combines great stability, permitting modification of the chemical structure of the substituents $R_1$, $R_2$ and $R_3$ while remaining unaltered, a high industrial yield and most important an ease of conversion thereof into the desired compounds. More particularly, as regards the final phase of obtainment of the end compounds (V), it is to be pointed out that quantitative yields are achieved, since the possible impurities of the reactants are the only obstacle.

It is furthermore noticeable that also the carbodiimide intermediate (VI) is novel and thus is an object of the present invention.

The following examples illustrate in a general and non-limiting manner the object of the present invention applied to the synthesis of niperotidine.

EXAMPLE 1A

O-para nitrophenyl-N-piperonyl-carbamate (Compound I where $R_1=H$, $R_2=(3,4\text{-methylenedioxy})\text{-benzyl}$, $Z=NO_2$)

In a flask are placed 10.08 g (0.05 mol) of paranitrophenylchloroformiate in 75 ml of anhydrous benzene (solution A). Separately is prepared an anhyrous benzene solution of 7.55 g (0.05 mol) of piperonylamine and 7 ml (0.05 mol) of triethylamine (solution B). Solution A is cooled to between 0° and 12° C. and solution B is introduced slowly. At the end of the introduction stirring is continued at room temperature for 4 hours. This intermediate (compound I) is not isolated and the next reaction is performed in the same reaction environment.

EXAMPLE 1B

N-[2-[[[5-[(dimethylamino)methyl]-2-furanyl]methyl]-thio]ethyl]-N'-(3,4 methylenedioxybenzyl)-urea (compound IIb)

To the solution obtained according to example 1A is added a benzene suspension (30 ml) containing 10.7 g (0.05 mol) of 2-[[[5-[(dimethylamino)methyl]-2-furanyl]-methyl]thio]ethylamine. The mixture obtained is kept heated while stirring for 6 hours. The crude substance is introduced in $H_2O/HCl$. The separated aqueous phase is washed with benzene, treated with $NaHCO_3$ and extracted again with $CHCl_3$. The organic solution is made anhydrous and evaporated until a raw oil is obtained which, when analyzed by mass spectromethy, NMR and IR, indicates the following structure.

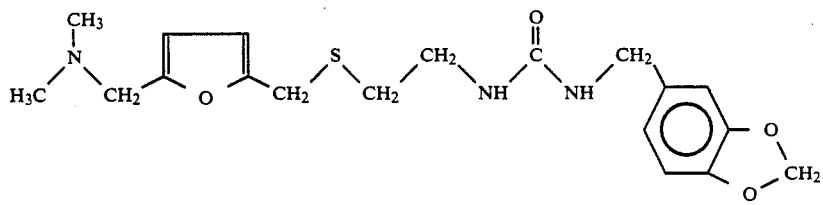

Compound IIb

Thin layer chromatography: Eluant: $CHCl_3/MeOH/36\% NH_3=9$ ml/0.5 ml/01 ml. Rf=0.5

EXAMPLE 1C

N-[2-[[[5-[(dimethylamino)methyl]-2-furanyl-]methyl]-thio]ethyl]-N'-(3,4methylenedioxybenzyl)-2-nitro-1,1-ethendiamine (Compound Vb).

In a flask, immersed in an ice and salt bath, nitromethane (3.5 g, 0.05 mol) and the urea previously prepared (19.5 g, 0.05 mol) are introduced; to the mixture is added methanol (50 ml) and a solution of sodium hydroxide (2.1 g) in an equal volume of cooled water, the latter solution slowly so that the temperature does not exceed 10°-15° C. Progressively as the addition is made a precipitate is formed, which can be diluted with further methanol. After one hour of stirring dilute hydrochloric acid is added until neutrality is reached, then water until slight clouding occurs. After a night at rest in a cool place the crystallized substance is collected and, if not sufficiently pure, is recrystallized from aqueous ethanol (16.9 g, 77.8%); m.p. 98°-120° C. (not corrected).

EXAMPLE 2A

O-phenyl-N-piperonylcarbamate (compound I with Z=H)

In a flask are placed 30 ml of chloroform and 15 g (0.06 mol) of phenylchloroformiate; in this solution is introduced piperonylamine (13 g, 0.086 mol) dissolved in 10 ml of chloroform and containing a stoichiometric quantity of pyridine or triethylamine.

The reaction takes place at between 5° C. and 25° C.

After terminating the introduction stirring is continued for 20 hours. The chloroform solution is washed repeatedly with water, then dried and concentrated. A white solid is obtained which is recrystallized from ethyl alcohol, filtered and dried. By crystallization are obtained 15 g of product with melting point 90°-92° C. The product is perfectly soluble in acetone and ethyl acetate; it is insoluble in water.

EXAMPLE 2B

N-(2-mercaptoethyl)-N'-(3,4 methylenedioxybenzyl) urea (compound IIIb)

6 g (0.022 mol) of phenylpiperonylcarbamate, prepared as in example 2A, are placed in pyridine and a heterogenous suspension is obtained. Separately a solution made in a nitrogen stream of 2.75 g (0.024 mol) of cysteamine hydrochloride and of NaOH (0.96 g, 0.024 mol) is prepared. The cysteamine solution thus obtained is added to the phenylpiperonylcarbamate solution and heated while stirring for 8 hours.

The solution is allowed to cool and a white crystalline product is precipitated. 100 ml of water are added and the solution is stirred for 2 hours and filtered. It is crystallized from acetone (50 ml) and then filtered and dried in an oven. 4.5 g of white product with melting point 192°-195° C. are obtained.

EXAMPLE 2C

N-[2-[[[5-[(dimethylamino)methyl]-2-furanyl]methyl]-thio]ethyl]-N-(3,4-methylenedioxybenzyl)-urea (compound IIb)

To absolute ethanol and dimethylformamide (20 ml) are added 1.32 g(0.044 mol) of NaH (80% by weight dispersed in oil).

To this mixture are added 5.08 g (0.02 mol) of N'(2 mercaptoethyl) N'(3,4-methylenedioxybenzyl) urea and after one hour of stirring at medium temperature are added 4.2 g (0.02 mol) of 5-(dimethylaminomethyl)-2-chloromethyl furan.

The reaction mixture is stirred and heated for 8 hours.

The reaction mixture is filtered to eliminate the NACl formed and taken up with an equal volume of $H_2O/HCl$. The solution is extracted with chloroform and the aqueous phase is washed several times with chloroform. The aqueous phase is then treated with $NaHCO_3$ up to neutral pH and again extracted with chloroform. The organic solution made anhydrous is evaporated to obtain 5.8 g of product (IIc) which when analyzed shows the same chemical and physical characteristics as the product obtained as in example 1B.

EXAMPLE 2D

N-[2-[[[5-[(dimethylamino)methyl]-2-furanyl]methyl]-thio]ethyl]-N'-(3,4 methylenedioxybenzyl)-2-nitro-1,1-ethlendiamine (Vb)

The product obtained in the example 2C is treated as in example 1C to obtain niperotidine.

EXAMPLE 3A

N-2-[(furfuryl)-thio]-ethyl-N'-(3,4-methylenedioxybenzyl)-urea (compound IVb)

To a pyridine solution (15 ml) of 5.44 g (0.02 mol) of O-phenyl-N-piperonylcarbamate another pyridine solution (15 ml) containing 3.14 (0.02 mol) of 2[[(2-furanyl)-methyl]thio]-ethylamine is added.

At the end of the introduction it is heated while stirring for 8 hours. At the end of the reaction the greater part of the pyridine is eliminated by distillation and then 100 ml of a solution of 1N hydrochloric acid are poured into the remaining raw reaction product. This solution is then extracted with chloroform and the organic solution obtained is made anhydrous and then evaporated to obtain 5.2 of oil which by mass spectrometry, NMR and IR, has the following structure.

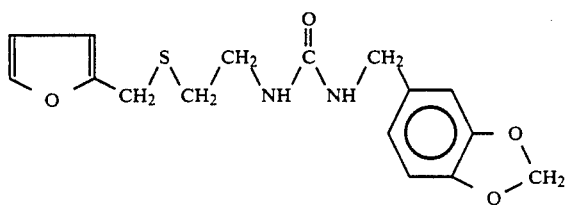

EXAMPLE 3B

N-[2-[[[5-[(dimethylamino)methyl]-2-furanyl]methyl]-thio]ethyl]-N'-(3,4 methylenedioxybenzyl)-urea (compound IIb)

6.7 g (0.02 mol) of product obtained as in example 3A are dissolved in absolute ethanol (50 ml) and to this solution are added 1.8 g (0.022 mol) of dimethylamine hydrochloride and 0.72 g (0.024 mol) of paraformaldehyde.

The solution is stirred and heated for between 2 and 5 hours. At the end the solvent is evaporated and 50 ml of water are poured in the reaction flask.

To this solution placed in a separating funnel are added further 5 ml of water containing 1 g of NaOH and the product is extracted with chloroform. The organic phase is made anhydrous and evaporated to obtain 4.3 g of product which upon analysis is the same as that obtained as in examples 1B and 2C.

EXAMPLE 3C

N-[2-[[[5-[(dimethylamino)methyl]-2-furanyl]methyl]-thio]ethyl]-N'-(3,4 methylenedioxybenzyl)-2-nitro-1,1-ethendiamine (Vb)

The product obtained from reaction 3B is treated as in example 1C to obtain niperotidine.

EXAMPLE 4A

N-[2-[[[5-[(dimethylamino)methyl]-2-furanyl]methyl]-thio]ethyl]-N'-(3,4 methylendioxybenzyl)carbodiimide

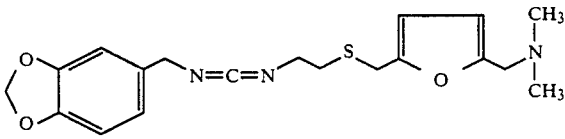

In a 200 ml three-necked flask 100 ml of dichloromethane are placed and 15 g of triphenylphosphine introduced. With an ice bath around the reaction flask the internal temperature is brought to approximately 0° C. Under continuous mechanical stirring the introduction of a solution of 3 ml of bromine dissolved in 10 ml of dichloromethane is started.

Introduction must be done very slowly with an internal temperature maintained between 0° C. and +5° C. When introduction of the bromide solution has been terminated the addition of 16.5 ml of triethylamine dissolved in 10 ml of dichloromethane is slowly and steadily started while keeping the temperature between 0° C. and +5° C.

Then the introduction of 15 g of urea dissolved in 30 ml of dichloromethane is started. Introduction takes place slowly at a temperature of between 0° C. and +5° C. The reaction is continued while stirring for approximately 2 hours after the introduction and the temperature rises slowly to room temperature.

The dichloromethane organic phase is washed with water for the removal of the inorganic salts contained, dried over sodium sulphate and then concentrated under vacuum to a small volume taking care not to exceed a bath temperature of 30° C. Then the dichloromethane solution is poured inot an ether solution (approximately 4 times the volume of the dichloromethane). Being almost entirely insoluble in ethyl ether the triphenylphospine and the triphenylphosphine oxide precipitate while all the carbodiimide (yield: 80% of theoretical), which is quite soluble in ethyl ether, passes into the ethereal phase.

The analitical assay is performed by IR spectroscopy checking the peak of the carbodiimide (2120 cm$^{-1}$) and by TLC (eluant: ethyl acetate/methanol/36% NH$_4$OH (9/0.5/0.1); detecting agent: solution of cerium phosphomolybdate).

EXAMPLE 4B

N-[2-[[[5-[(dimethylamino)methyl]-2-furanyl]methyl]-thio]ethyl]-N'-(3,4 methylenedioxybenzyl)-2-nitro-1,1-ethendiamine (Vb)

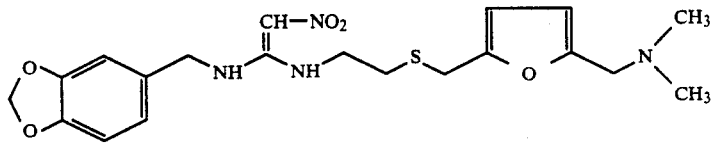

In 40 ml of dimethylformamide are introduced slowly while stirring 1.2 g (1 mol +20%) of 80% NaH in an oily suspension, the addition being performed by portions. When the introduction has been terminated while stirring, 5.1 ml (3 mol) of nitromethane are introduced slowly. The reaction is slightly exothermic. Stirring is continued at room temperature until the solution turns intense yellow. This coloration is completed within 3-4 hours at a temperature of between 20° and 30° C.

In the nitromethane solution prepared as explained above a solution of 10 g (1 mol) of carbodiimide in dimethylformamide (20 ml) is introduced slowly at room temperature.

When introduction has been completed the mixture is heated to 75°-80° C. for approximately 2 hours, monitoring the reaction by TLC (eluant:ethyl acetate/methanol/35% NH4OH (9/0.5/0.2); detecting agent cerium phosphomolybdate). Raw niperotidine is obtained with a yield of 85% of theoretical. The reaction mixture is concentrated under vacuum from the dimethylformmide and then the raw niperotidine passes to the purification process.

EXAMPLE 5A

N,N'-di-[N-(3,4-methylenedioxybenzyl)-carbamoyl]2,2'-dithiobisethanamine.

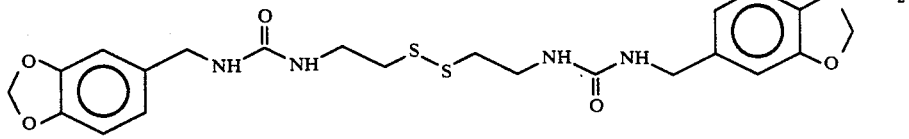

In a 500 ml 3-necked flask equipped with a mechanical stirrer are placed 40 g of O-phenyl-N-(3,4-methylenedioxybenzyl)-carbamate and 150 ml of pyridine. The reaction mixture is then brought to 45° C.

An aqueous solution (32 ml) containing 16.5 g of cystamine dihydrochloride and 5.88 g of sodium hydride is prepared spearately.

The aqueous solution is dripped into the pyridine solution and at the end the reaction mixture is heated to 90°-95° C. for approximately 20 hours. After cooling with precipitation of a white substance the reaction mixture is poured into 400 ml of water and after 2 hours of vigorous stirring the precipitated substance is filtered and washed with water acidulated with acetic acid.

The product is repeatedly mashed in water and filtered to eliminate traces of pyridine, then it is poured into 60 ml of acetone to eliminate traces of phenol. It is filtered and vacuum dried at 60°-70° C. for 12 hours.

33 g of product are obtained for a yield of 88.7% and the melting point is 181°-183° C.

EXAMPLE 5B

N-(2-mercaptoethyl)-N'-(3,4-methylendioxy benzyl)-urea (III)

500 ml of glacial acetic acid and 50 g of the ditiourea, as obtained in Example 5A, are charged into a 1000 ml four necked flask, and the reaction mixture is heated under mechanical stirring up to complete dissolution of the product (80° C.).

Once the dissolution is completed, 13 g of metal zinc powder are added and the reaction mixture is vigorously stirred for 5 hours at 100° C. temperature.

After cooling 38 ml of 36% HCl are added to solubilize the reaction mass.

The unreacted zinc is filtered under vacuum and the clear solution is poured into 2500 ml water, nitrogen being bubbled to eliminate possible traces of oxygen.

The mixture is stirred for 30 minutes and filtered under vacuum. The obtained product is washed with further 2500 ml of water and is dried in oven under vacuum at 100° C. for 8 hours. 49.7 g of compound (iII) (yield 98%) are obtained having the foreseen chemical and physical properties.

What is claimed is:

1. A process for the synthesis of niperotidine which comprises the following steps:

(a) reacting a piperonylamine of the formula

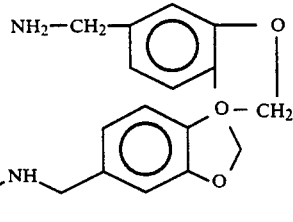

with a compound of the formula

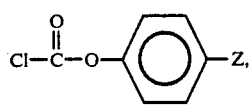

wherein Z presents H, NO2 or a halogen, to form a carbamate of the formula

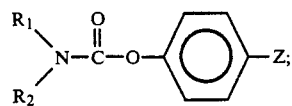

wherein $R_1$ is hydrogen and $R_2$ is piperonyl, (b) reacting the carbamate with $H_2N—(CH_2)_2—S—S—(CH_2)_2—NH_2$ to form a disulfide of the formula,

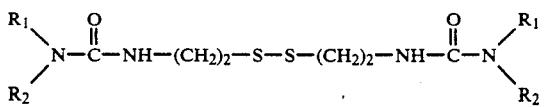

(c) reducing the disulfide with metallic zinc and acetic acid to form a mercaptan of the formula

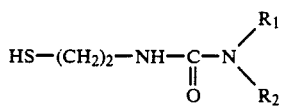

(d) reacting the mercaptan with 5-N,N'-dimethylaminomethyl)-2-chloromethylfuran to form a urea of the formula

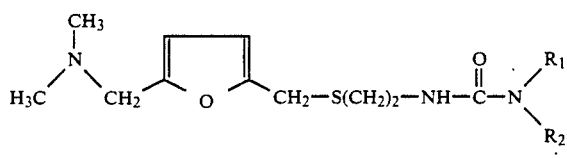

(e) reacting the urea with triphenylphosphine in presence of bromine and an acid acceptor to form the corresponding carbodiimide of the formula

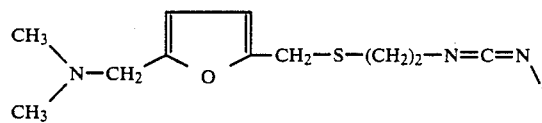

(f) and reacting the carbodiimide with nitromethane, in the present of a strong base, to form niperotidine.

2. A process in accordance with claim 1, wherein step (a) is effected in a organic solvent or mixture of organic solvents at a temperature of between 0° and 25° C.

3. A process in accordance with 1, wherein step (a) is effected in benzene and in the presence of triethylamine.

4. A process in accordance with claim 1, wherein step (a) is effected in chloroform and in the presence of pyridine or triethylamine.

5. A process in accordance with claim 3, wherein the reaction mixture is used as is in the next step (b).

6. A process in accordance with claim 4 wherein the carbamate is isolated before it is used in step (b).

7. A process in accordance with claim 1, wherein step (b) is effected in an organic solvent or in a mixture of an organic solvent and water at a temperature between room temperature and the boiling point of the solvent.

8. A process in accordance with claim 7, wherein the organic solvent is pyridine.

9. A process in accordance with claim 1, wherein the mercaptan is activated with a base and reacted with the 5-(N,N'-dimethylaminomethyl)-2-chloromethylfuran in a polar solvent.

10. A process in accordance with claim 9, wherein the base is sodium hydride.

11. A process in accordance with claim 9, wherein the polar solvent is dimethylformamide or a low boiling aliphatic alcohol.

12. A process in accordance with claim 1, wherein step (e) is effect out in an aprotic solvent.

13. A process in accordance with claim 12, wherein the aprotic solvent is a chlorinated hydrocarbon.

14. A process in accordance with claim 1, wherein step (e) is effected at a temperature between 5° and 10° C.

15. A process in accordance with claim 1, wherein a molar excess of triphenylphosphine is present in step (c).

16. A process in accordance with claim 15, wherein the molar excess is 1.5 molar.

17. A process in accordance with 1, wherein the acid acceptor in step (e) is triethylamine.

18. A process in accordance with claim 1, wherein step (f) is effected in a polar aprotic solvent.

19. A process in accordance with claim 18, wherein the polar solvent is a bipolar aprotic solvent.

20. A process in accordance with claim 1, wherein the strong base in step (f) is sodium hydride.

21. A process in accordance with claim 1, wherein step (f) is effected by heating the reaction mixture to a temperature of 75°–80° C.

22. A process in accordance with claim 1, wherein the reaction step (b) is effected in pyridine at a temperature of 40°–50° C.

* * * * *